United States Patent [19]

Benson et al.

[11] 4,096,254
[45] Jun. 20, 1978

[54] METHOD OF TREATING THE SYMPTOMS OF MENOPAUSE AND OSTEOPOROSIS

[75] Inventors: Harvey D. Benson, Cincinnati; Joyce Francis Grunwell, Hamilton; John O'Neal Johnston, Cincinnati, all of Ohio; Vladimir Petrow, Chapel Hill, N.C.

[73] Assignee: Richardson-Merrell Inc., Wilton, Conn.

[21] Appl. No.: 770,400

[22] Filed: Feb. 22, 1977

Related U.S. Application Data

[63] Continuation-in-part of Ser. No. 684,949, May 10, 1976, abandoned.

[51] Int. Cl.² .................. C07J 1/00; A61K 31/56
[52] U.S. Cl. ................................ 424/242; 424/243
[58] Field of Search ........................ 424/242, 243

[56] References Cited
U.S. PATENT DOCUMENTS 4,022,769  5/1977  Grunwell et al. ............... 429/242

Primary Examiner—Elbert L. Roberts

Attorney, Agent, or Firm—L. Ruth Hattan; Eugene O. Retter; George W. Rauchfuss, Jr.

[57] ABSTRACT

Compounds of the following general formula are useful in treating the symptoms of menopause and osteoporosis:

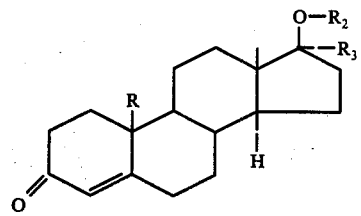

wherein R is —CHO or —$CH_2OR_1$; each of $R_1$ and $R_2$ is hydrogen, alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched or cycloalkylcarbonyl wherein the cycloalkyl moiety has from 5 to 10 carbon atoms; $R_3$ is hydrogen; or $R_2$ and $R_3$ together form a double bond between the 17-position carbon atom and the oxygen atom.

18 Claims, No Drawings

METHOD OF TREATING THE SYMPTOMS OF MENOPAUSE AND OSTEOPOROSIS

This application is a continuation-in-part of copending U.S. application Ser. No. 684,949, filed May 10, 1976, now abandoned.

FIELD OF THE INVENTION

This invention relates to methods of treating the symptoms of menopause and osteoporosis and pharmaceutical compositions useful for said treatment.

BACKGROUND OF THE INVENTION

Menopause is the transitional phase in a woman's life when menstrual function ceases and can result from natural or induced changes in the body. Natural menopause results from declining ovarian function due to aging of the ovaries which become atrophic and usually occurs between ages 40 and 50. Occasionally ovarian function ceases prior to age forty resulting in premature menopause.

It is believed that the symptoms of menopause are due primarily to estrogen deficiency since when menopause occurs there is a marked decrease in ovarian estrogen production and since the administration of estrogens, for example, diethylstibestrol, conjugated estrogens or estradiol provide a specific and effective manner of treatment. However, it is becoming increasingly apparent that estrogenic products currently in use possess certain undesirable side effects which must be set against the undoubted benefits resulting from their use. For example, diethystilbestrol, a once widely used and well established estrogen, has been implicated as possibly being responsible for vaginal cancer and adenosis of the female offspring of pregnant women treated with the compound (Lancet 1975, 1960). Also, ethinyl estradiol and mestranol, which represent estrogenic components in current oral contraceptives are now known to be involved in certain serious side effects associated with oral contraceptives including depression, (Nature 243, 58 (1973)), hypertension (Am. J. Obstet. Gynecol. 112, 912 (1972)), carbohydrate and lipid abnormalities (Lancet 1969, Oct. 11, 783), interference with blood clotting mechanism resulting in thrombosis and stroke (Ann. Intern Med. 72, 111 (1970)), and jaundice (Am. J. Obstet. Gynecol. 119, 165 (1974)). Also, the administration of estrogens to post-menopausal women has been implicated as a cause of endometrial cancer (Science 191, 838 (1976)). Consequently, there is a need for an improved method of treating menopause.

The present invention provides a novel and improved method of treating the symptoms of menopause and osteoporosis which comprises administering androstene compounds described more fully hereinbelow. Some of the compounds employed in the present invention, for example, 19-hydroxyandrost-4-ene-3,17-dione and the 19-oxo derivative thereof have been involved in numerous in vitro studies wherein their role in the metabolism of androgens has been investigated. Additionally, 19-hydroxyandrost-4-ene-3,17-dione is reported to have been administered to two healthy male subjects each 21 years of age (J. Clin. Endocrinol. Metab. 28, 1401 (1968)). Also, 3-oxo-17β-hydroxyandrost-4-en-19-al has been reported in U.S. Pat. No. 3,235,573 issued Feb. 15, 1966 and U.S. Pat. No. 3,449,381 issued June 10, 1969 wherein the utilities disclosed are anabolic-androgenic activity, inhibition of pituitary gonadotrophins and adrenocorticotrophin, antiestrogenic, blood, liver and adrenal cholesterol lowering properties, control of fertility and psychotic changes, and appetite stimulants. To applicant's knowledge, the use of the compounds employed in the present invention in the treatment of the symptoms of menopause or osteoporosis has not been taught or suggested heretofore.

SUMMARY OF THE INVENTION

This invention relates to a method of treating the symptoms of menopause and osteoporosis by administering a compound of the following general formula:

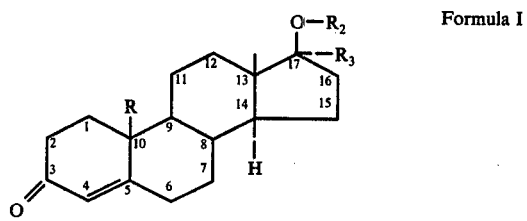

Formula I wherein R is —CHO or —CH$_2$OR$_1$; each of R$_1$ and R$_2$ is hydrogen, alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched or cycloalkylcarbonyl wherein the cycloalkyl moiety has from 5 to 10 carbon atoms; R$_3$ is hydrogen; or R$_2$ and R$_3$ together form a double bond between the 17- position carbon atom and the oxygen atom. This invention also relates to pharmaceutical preparations suitable for use in treating the symptoms of menopause.

DETAILED DESCRIPTION OF INVENTION

The present invention relates to a method of treating the symptoms resulting from or associated with the occurrence of menopause which begin with menopause and continue in the post-menopausal woman such symptoms being many and well documented. The primary symptoms of menopause are hot flashes, or hot flushes, inappropriate or excessive perspiration, atrophic vaginitis, changes in the skin, primarily wrinkling through dehydration of the skin, particularly exposed facial skin and a thinning of the epidermis and loss of rete ridges, and post-menopausal osteoporosis or osteopenia. Other symptoms of menopause include chilling sensations, paresthesias, and muscle cramps. The present invention also relates to the treatment of osteoporosis in warm blooded animals and mammals for example, dogs, cats, rats, bovine cows, horses and humans including but not limited to post-menopausal women. The methods of the present invention offer distinct advantages over the usual methods of treating the symptoms of menopause and osteoporosis, that is, estrogen therapy, in that the compounds employed do not result in certain deleterious side effects resulting with estrogen therapy as will become more apparent hereinafter.

In the compounds of general Formula I the term alkylcarbonyl is taken to mean a group of the structure

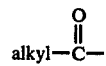

wherein the alkyl moiety has from 1 to 20 carbon atoms and can be a straight chain or a branched chain. Illustrative examples of the alkyl moiety in the substituent alkylcarbonyl group are methyl, ethyl, n-propyl, isopropyl, n-butyl, sec-butyl, tert-butyl, n-pentyl, neopentyl, pivalyl, hexyl, heptyl, octyl, 2,4-dimethyloctyl, undecyl, 9-methylundecyl, pentadecyl, hexadecyl, dodecyl, 2,4,6-trimethyldecyl, heptadecyl, decyl, octadecyl, nonadecyl and didecyl.

The term benzoyl as used in reference to the compounds of general Formula I is taken to mean the group

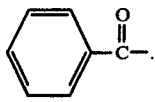

The term phenylalkylcarbonyl as used in reference to the compounds of general Formula I is taken to mean a substituent group of the structure

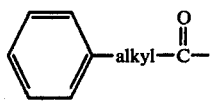

wherein the alkyl moiety, which may also be referred to as an alkylene moiety, has from 1 to 6 carbon atoms and can be a straight chain or a branched chain. Illustrative examples of the alkyl moiety in the substituent phenylalkylcarbonyl group are methyl, ethyl, n-propyl, n-butyl, n-pentyl, hexyl, isopropyl, sec-butyl, tert-butyl and neopentyl.

Illustrative examples of cycloalkylcarbonyl groups which $R_1$ and $R_2$ may be are cyclopentanecarbonyl, cyclohexanecarbonyl, cyclooctanecarbonyl, 1- or 2-norbornanecarbonyl, and 1- or 2-adamantanecarbonyl.

It is apparent from the foregoing general Formula I that the compounds employed in the instant invention are androst-4-ene-3,17-diones having a —CH$_2$OR$_1$ or —CHO group at the 10β-position as represented respectively by the following general Formulas II and III, or are 17β-hydroxyandrost-4-en-3-one derivatives or esters thereof as defined by $R_2$ having a —CH$_2$OR$_1$ or —CHO group present at the 10β-position as represented respectively by the following general Formulas IV and V:

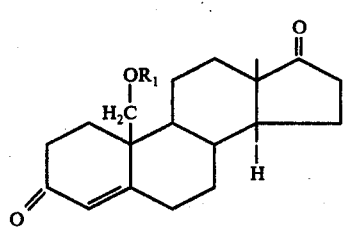

Formula II

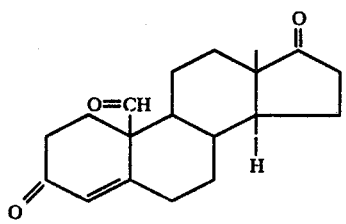

Formula III

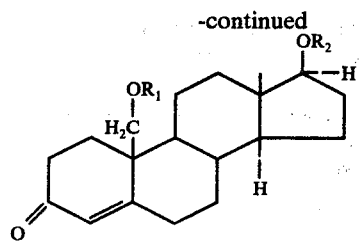

Formula IV

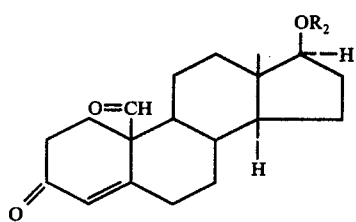

Formula V

In general Formulas II to V $R_1$ and $R_2$ are hydrogen or alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched or cycloalkylcarbonyl wherein the cycloalkyl moiety has from 5 to 10 carbon atoms as defined hereinabove.

The use of the compounds as represented by each of general Formulas II and III in the treatment of the symptoms of menopause and osteoporosis represent preferred embodiments of this invention. The use in the treatment of the symptoms of menopause and osteoporosis of the compounds of general Formula III represents a more specifically preferred embodiment of this invention. Other embodiments of this invention are the use of the compounds as represented by general Formulas IV and V in the treatment of the symptoms of menopause and osteoporosis with the use of the compounds of general Formula IV wherein $R_1$ and $R_2$ each represent hydrogen and the compounds of general Formula V where $R_2$ represents hydrogen being more preferred embodiments.

Illustrative examples of compounds employed in the present invention are 17β,19-bis-(1-oxopropoxy)androst-4-en-3-one, 17β,19-bis-(1-oxodidecyloxy)androst-4-en-3-one, 17β,19-dihydroxyandrost-4-en-3-one, 19-hydroxy-17β-(1-oxopropoxy)androst-4-en-3-one, 19-hydroxy-17β-(1-oxohexadecyloxy)androst-4-en-3-one, 19-acetoxyandrost-4-ene-3,17-dione, 19-acetoxy-17β-hydroxyandrost-4-en-3-one, 3-oxo-17β-hydroxyandrost-4-en-19-al, 19-(1-adamantanylcarbonyloxy)androst-4-ene-3,17-dione, 19-(1-norbornylcarbonyloxy)-androst-4-ene-3,17-dione, 19-(1-cyclopentylcarbonyloxy)-androst-4-ene-3,17-dione, 3,17-dioxoandrost-4-en-19-al and 3-oxo-17β-(1-adamantanylcarbonyloxy)androst-4en-19-al.

In treating the symptoms of menopause the compounds employed in the present invention can be administered in various manners to achieve the desired effect. The compounds can be administered alone or in the form of pharmaceutical preparations to the patient being treated either orally, parenterally, that is, subcutaneously or intramuscularly, or topically or intravaginally. The amount of compound administered will vary with the patient. For oral administration the effective amount, that is, the amount of compound effective in treating the symptoms of menopause, ranges from 0.01 mg/kg up to 3.0 mg/kg, and preferably from 0.1 mg/kg to 1.0 mg/kg; for parenteral administration, that is, subcutaneous or intramuscular administration, from 0.01 mg/kg up to 3.0 mg/kg and preferably from 0.1 mg/kg to 1.0 mg/kg. For topical or intravaginal administration the amount of compound effective in treating the symptoms of menopause employed in the present invention on a percent basis is from 0.001% to 5% and preferably from 0.005% to 1%. As used herein the term patient is taken to mean a female having symptoms of menopause in need of treatment.

In the treatment of osteoporosis the compounds employed in the present invention can be administered alone or in the form of pharmaceutical preparations to the patient being treated either orally or parenterally, that is, for example, subcutaneously or intramuscularly. The amount of compound employed will vary with the patient to be treated and the severity of the condition. The effective amount of compound to be administered orally in treating osteoporosis in humans will vary from about 0.01 mg/kg up to 3.0 mg/kg, and preferable from about 0.1 mg/kg to 1.0 mg/kg. For parenteral administration the effective amount of compound to be administered in treating osteoporosis in humans will vary from about 0.01 mg/kg up to 3 mg/kg and preferably from 0.1 mg/kg to 1.0 mg/kg. The effective amount of compound to be employed in treating osteoporosis in warm blooded animals and mammals other than humans will vary from about 0.01 mg/kg to about 30 mg/kg, preferably about 0.1 mg/kg to 10 mg/kg and most preferably about 0.1 mg/kg to 3 mg/kg. As used herein in reference to the treatment of osteoporosis the term patient is taken to mean warm blooded animals, mammals, for example, dogs, cats, rats, bovine cows, horses and humans. Osteoporosis in the art is a recognized bone disorder or skeletal disorder associated with loss of hydroxyapatite, that is, calcium phosphate complexes and protein matrix which is prevalent in, although not limited to, aged patients.

For oral administration the compounds can be formulated into solid or liquid preparations such as capsules, pills, tablets, troches, powders, solutions, suspensions or emulsions. The compounds can be applied in the form of an aerosol containing finely divided particles of the active ingredient or a solution, suspension or emulsion of the active ingredient. The solid unit dosage forms can be of the conventional type. Thus, the solid form can be a capsule which can be of the ordinary gelatin type containing a compound of general Formula I and a carrier, for example, lubricants and inert filler such as lactose, sucrose, and corn starch. In another embodiment the compounds of general Formula I can be tableted with conventional table bases such as lactose, sucrose and corn starch or gelatin, disintegrating agents such as potato starch or alginic acid, and a lubricant such as stearic acid or magnesium stearate.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable or synthetic origin, for example, peanut oil, soybean oil, and mineral oil. In general water, saline, aqueous dextrose, and related sugar solutions, ethanols and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

For topical administration the formulated active ingredient can be applied directly to the site requiring treatment or it can be applied to a mucosal membrane such as the oral or nasal mucosa. Applicator sticks carrying the formulation may be employed in administering the compounds. The topical formulation can be, for example, in the form of a solution, suspension, emulsion and cream of either the oil in water or water in oil type, ointment, paste, jelly, paint or powder. Suitable bases for the topical preparation may be of any conventional type such as oleaginous bases, for example, olive oil, cottonseed oil, petrolatum, white petrolatum, mineral oils, silicones, such as, dimethylpolysiloxane or methyl phenylpolysiloxane, lanolins, polyethylene glycol, glyceryl monostearate, methyl cellulose and hydroxy methyl cellulose. The topical formulation may contain pharmaceutically acceptable surfactants, wetting agents, dispersing agents, emulsifiers, penetrants, emollients, detergents, hardeners, preservatives, fillers, antioxidants, perfumes, cooling agents, such as, menthol, soothing agents, such as, camphor, or coloring agents, such as zinc oxide. Aerosol preparations of a solution, suspension or emulsion containing the active ingredient or an aerosol containing the active ingredient in the form of a finely ground powder can also be employed for topical administration. The aerosols may be packaged in a pressurized aerosol container together with a gaseous or liquified propellant, for example, dichlorodifluoromethane, dichlorodifluoromethane with dichlorodifluoroethane, carbon dioxide, nitrogen, or propane with the usual adjuvant such as cosolvent and wetting agents as may be necessary or desirable. The compounds may also be administered in a nonpressurized form such as in a nebulizer or atomizer.

When topical treatment is desired, or when a more rapid effect is desired it will generally be more convenient to use compounds of general Formula I wherein each of $R_1$ and $R_2$ is hydrogen.

Following are illustrative pharmaceutical formulations which may be employed in practicing the present invention:

| Solution | | |
|---|---|---|
| 3,17-Dioxoandrost-4-en-19-al | 0.85 | g |
| Alcohol | 78.9 | ml |
| Isopropyl Myristate | 5.0 | g |
| Polyethylene Glycol 400 | 10.0 | g |
| Purified Water qs ad | 100 | ml | combine the alcohol, isopropyl myristate and polyethylene glycol 400 and dissolve the drug substance therein. Add sufficient purified water to give 100 ml.

| Gelled Solution | | |
|---|---|---|
| 3,17-Dioxoandrost-4-en-19-al | 0.85 | g |
| Alcohol | 78.9 | ml |
| Isopropyl Myristate | 5.0 | g |
| Polyethylene Glycol 400 | 10.0 | g |

| -continued Gelled Solution | | |
|---|---|---|
| Carbopol 940 (Carboxypolymethylene) | 0.75 | g |
| Triethylamine | qs | |
| Purified Water qs ad | 85 | g |

Disperse the Carbopol 940 in the isopropyl myristate. To 38 ml of alcohol add 7 ml of purified water and the polyethylene glycol 400 and mix. Combine the two phases and mix until well dispersed. Add sufficient triethylamine to give a neutral pH. Dissolve the drug substance in the balance of the alcohol and mix well into the batch. Add and mix sufficient purified water to provide 85 g of finished product.

| Applicator Stick Solution | | |
|---|---|---|
| 3,17-Dioxoandrost-4-en-19-al | 0.85 | g |
| Absolute Alcohol | 75 | ml |
| Polyethylene Glycol 400 | 10.0 | g |
| Isopropyl Myristate | 5.0 | g |
| Stearic Acid | 4.3 | g |
| Sodium Hydroxide | 0.55 | g |
| Purified Water qs ad | 85 | g |

Combine the absolute alcohol, polyethylene glycol 400 and isopropyl myristate and dissolve the drug substance therein. Add the stearic acid and heat the mixture to about 65° C. Dissolve the sodium hydroxide in a small amount of water, add and mix. Add sufficient water to provide 85 g of finished product. Pour into suitable moulds and allow to solidify.

| Aerosol Foam | | |
|---|---|---|
| 3,17-Dioxoandrost-4-en19-al | 1.0 | g |
| Propylene Glycol | 96.0 | g |
| Emulsifying Wax NF XIV | 3.0 | g |
| Dichlorodifluoromethane:cryofluorane (20:80) | 6.9 | g |

Dissolve the drug substance in the propylene glycol. Add the emulsifying wax and heat to approximately 70° C. Stir while cooling to room temperature. Charge a suitable aerosol unit with this concentrate and 6.9 g of dichlorodifluoromethane; cryofluorane (20:80).

| Tablet | For 15,000 | |
|---|---|---|
| 3,17-Dioxoandrost-4-en-19-al Fine Powder | 75 | g |
| Lactose | 1.216 | Kg |
| Corn Starch | 0.3 | Kg |

Mix the active ingredient, the lactose and corn starch uniformly. Granulate with 10% starch paste. Dry to a moisture content of about 2.5%. Screen through a No. 12 mesh screen. Add and mix the following:

| Magnesium Stearate | 0.015 Kg |
|---|---|
| Corn Starch qs ad | 1.725 Kg |

Compress on a suitable tablet machine to a weight of 0.115 g/tablet or 0.230 g/tablet.

| Soft Gelatin Capsule | | |
|---|---|---|
| 3,17-Dioxoandrost-4-en-19-al | 0.25 | Kg |
| Polysorbate 80 | 0.25 | Kg |

| -continued Soft Gelatin Capsule | | |
|---|---|---|
| Corn Oil qs ad | 25.0 | Kg |

Mix and fill into 50,000 soft gelatin capsules.

| IM Depot Injection | | |
|---|---|---|
| Each 1 ml contains the following: | | |
| Anhydrous Chlorobutanol | 5.0 | mg |
| Aluminum Monostearate | 50.0 | mg |
| Peanut Oil qs ad | 1.0 | ml |

Dissolve or disperse the ingredients in the peanut oil.

| Depot-Implant | | |
|---|---|---|
| 3,17-Dioxoandrost-4-en-19-al | 5 | mg |
| Catalyst qs | 240 | mg |

Disperse the drug substance in the fluid dimethylsiloxane. Add the catalyst and cast into a suitable monolytic structure.

Alternatively, the drug substance may be enclosed by a pre-cast polydimethylsiloxane envelope.

Alternatively, the drug substance may be dispersed in a suitable amount of hydroxyethyl acrylate subsequently polymerized and cross-linked by the addition of ethylenedimethacrylate, and an oxidizing agent, to yield a 3-dimensional ethylene glycomethacrylate mouldable gel (Hydron).

| Topical Cream, Vanishing, w/w | |
|---|---|
| | % w/w |
| 3,17-Dioxoandrost-4-en-19-al | 1 |
| Stearic Acid | 15 |
| Isopropyl Myristate | 2 |
| Sorbitan Monostearate | 1.8 |
| Polyoxyethylene Sorbitan Monostearate | 2.3 |
| Propylene Glycol | 5 |
| Methylparaben | 0.025% |
| Propylparaben | 0.015% |
| Purified Water | qs |

| IM Injection | | |
|---|---|---|
| A. Oil Type: | | |
|    3,17-Dioxoandrost-4-en-19-al | 25 | mg |
|    BHA, BHTaa | 0.01% | w/v |
|    Peanut Oil or Sesame Oil qs | 1.0 | ml |
| B. Suspension Type: | | |
|    3,17-Dioxandrost-4-en-19-al micronized | 25 | mg |
|    Sodium Carboxymethylcellulose | 0.5% | w/v |
|    Sodium Bisulfite | 0.02% | w/v |
|    Water for injection, qs | 1.0 | ml |

| Buccal or Sublingual Tablet | |
|---|---|
| 3,17-Dioxoandrost-4-en-19-al | 1% |
| Calcium Stearate | 1% |
| Calcium Saccharin | 0.02% |
| Granular Mannitor | qs |

Mix and compress on a suitable tablet machine to a weight of 0.115 g/tablet.

Medicated Tampon 50 mg of 3,17-dioxoandrost-4-en-19-al in a volatile solvent, such as, ethylalcohol is applied to a vaginal tampon of cellulosic or related composition and allowed to dry therein.

| Donor Pessary | | |
|---|---|---|
| 3,17-Dioxoandrost-4-en-19-al | 50 | mg |
| Dimethylsiloxane | 5 | g |
| Catalyst, suitable | qs | |

Disperse the active ingredient in the fluid dimethylsiloxane, add the catalyst and cast into a suitable structure for vaginal insertion, such as, a doughnut shape.

| Vaginal Cream | % w/w |
|---|---|
| 3,17-Dioxoandrost-4-en-19-al | 1.0 |
| Lactose | 5.0 |
| Lactic Acid, 50% | 1.3 |
| Sorbitol Solution, 70% | 15.0 |
| Stearic Acid | 10.0 |
| Diglycol Stearate | 7.0 |
| Polysorbate 80 USP | 1.0 |
| Benzoic Acid | 0.1 |
| Purified Water | qs |

| Vaginal Insufflation Powder | |
|---|---|
| | %w/w |
| 3,17-Dioxoandrost-4-en-19-al, micronized | 1% |
| Silicon Dioxide Anhydrous | 0.5% |
| Corn Starch and Lactose, Fine Powder | qs (of each) |

Administration of the compounds of general Formulas I to V to a human patient in need thereof in the effective amounts described hereinabove results in the effective treatment of the symptoms of menopause and osteoporosis without the occurence of certain deleterious side effects reported to occur with the administration of estrogenic agents including uterine endometrial growth in females and thrombotic effects, such as blood clotting. Administration of the compounds employed in the present invention in amounts higher than that specified above as an effective amount may result in these deleterious estrogenic side effects.

Since with the occurrence of menopause there is a marked reduction of ovarian estrogen production resulting in a gap in the reproductive hypothalamo-pituitary-ovarian feedback system there is an increase in circulating levels of gonadotrophins, that is, follicle stimulating hormone (FSH) and leutinizing hormone (LH). Also, it is believed that the increased amounts of FSH and LH are responsible for the hot flashes or hot flushes that occur with menopause. Monitoring the amount of gonadotrophins present in the patient provides an important and useful means of diagnosing menopause and finding a proper therapy. Estrogens, which are frequently used in treating the symptoms of menopause, fill in the gap in the reproductive feedback system resulting in a decrease in the amount of gonadotrophins present. The effectiveness of other agents which could serve as a replacement for ovarian estrogens could be measured by monitoring gonadotrophin level or by measuring the weight of the pituitary which may change as gonadotrophin production is modified.

The utility of the compounds employed in the present invention can be demonstrated by administering the test compound to hemicastrated immature rats either male or female and measuring the levels of gonadotrophins, the weight of the pituitary or the weights of the remaining gonad and secondary sex organs, such as, the ventral prostate, seminal vesicles and uterus. It is known that upon hemicastration of immature rats gonadotrophin levels increase with a resultant hypertrophy of the remaining gonad. Compounds which mimic estrogens result in decreased levels of gonadotrophins, a change in the weight of the pituitary and decreased gonadal and secondary sex organ weights. It has been found that compounds employed in the present invention act in a manner similar to that of estrogens in their effects on the foregoing enumerated parameters. Although the compounds employed in the present invention mimic estrogens in their effect on the hypothalamo-pituitary-gonadal feedback mechanism and consequent effects on gonadotrophin levels and sex organ weights demonstrating that the compounds afford a novel method for treating the symptoms of menopause said method offers the further advantage that the compounds employed at the effective dosages enumerated hereinabove do not result in certain deleterious side effects associated with estrogen therapy, such as, uterine growth and interference with blood clotting mechanisms.

The data contained in the following Table I indicate that 3,17-dioxoandrost-4-en-19-al does not bind in vitro with the estrogen receptor of uterine estrogen target tissue. This binding is the first step necessary for hormonal action. To obtain these data female hamsters were ovariectomized and uterine cytosol was prepared 24 to 48 hours post surgery. Concentrations of $4 \times 10^{-6}$ to $4 \times 10^{-10}$ molar were compared for competitive bindings of $H^3$-estradiol-17$\beta$-labeled cytosol receptor sites according to the methods of Leavitt et al., Endocrin. 94, 1041 (1974) and Korenman, J. Clin. Endocrin. and Metab. 28, 127 (1968). The relative binding was compared with estradiol which was equated to 100.

TABLE 1

| Uterine Cytosol Affinity | |
|---|---|
| Treatment | Relative Estrogen Binding Affinity |
| Estradiol | 100 |
| Estrone | 22 |
| Estriol | 10 |
| 3,17-Dioxoandrost-4-en-19-al | 0.01 |

The lack of estrogen binding affinity of 3,17-dioxoandrost-4-en-19-al supports the finding of lack of certain estrogenic side effects of the compounds employed in the present invention.

That the compounds employed in the present invention have no significant uterotrophic effect as compared to estradiol is reflected by the data in the following Table II which were generated from ovariectomized rats treated with 3 $\mu$g per rat per day of either estradiol or 3,17-dioxoandrost-4-en-19-al for 20 days.

TABLE II

| Uterotrophic Activity | | |
|---|---|---|
| Treatment | Dose ($\mu$g/rat) | Uterine Wt. (mg ± S.E.M.) |
| Control | — | 33.7 ± 1.7 |
| Estradiol | 3.0 | 206.6 ± 8.1* |
| 3,17-Dioxoandrost-4-en-19-al | 3.0 | 41.1 ± 4.7 |

*Significantly different from control; p ≦0.01

The data contained in Tables I and II demonstrate that 3,17-dioxoandrost-4-en-19-al has no systemic estrogenic effect on uterine weight or vaginal cornification which occurs with estradiol treatment.

It has also been found that the compounds employed in the present invention have no thrombotic potential. For example, 3,17-dioxoandrost-4-en-19-al was given subcutaneously to ovariectomized albino rats for seven days at either 0.1 or 3.0 mg/kg. Body weight and uterine weights were measured. Blood samples were taken and the effect on thrombotic potential determined through measurements of anti-thrombin III activity, ethanol gel tests, (fibrin monomer level), protamine sulfate test (fibrin degradation products), adenosinediphosphate and collagen induced platelet aggregation. Anti-thrombin activity was not affected nor was increased fibrin monomer or fibrin degradation product level detected. Platelet aggregation was not significantly changed.

Many of the compounds employed in the present invention are known in the art or are commercially available. For example, 19-hydroxyandrost-4-ene-3,17-dione, 17β,19-dihydroxyandrost-4-en-3-one, 19-hydroxy-17β-(1-oxoethoxy)-androst-4-en-3-one, 19-hydroxy-17β-(1-oxobenzyloxy)androst-4-en-3-one and 3-oxo-17β(1-oxobenzyloxy)androst-4-en-19-al are commercially available.

The esters of the compounds employed in the present invention, that is, compounds wherein either or both of $R_1$ and $R_2$ are alkylcarbonyl wherein the alkyl moiety has from 1 to 20 carbon atoms and is straight or branched, cycloalkylcarbonyl wherein the cycloalkyl moiety has from 5 to 10 carbon atoms, benzoyl and phenylalkylcarbonyl wherein the alkyl moiety has from 1 to 6 carbon atoms and is straight or branched can be prepared as follows although other methods may also be employed. Ester derivatives of 19-hydroxyandrost-4-ene-3,17-dione and bis-ester derivatives of 17β,19-dihydroxyandrost-4-en-3-one are prepared by reacting the corresponding 19-hydroxy or 17β,19-dihydroxy compound with an appropriate acid anhydride of the formula

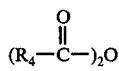

or acid chloride of the formula

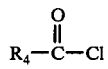

wherein $R_4$ is an alkyl group of from 1 to 20 carbon atoms and is straight or branched, a cycloalkyl group of from 5 to 10 carbon atoms, phenyl or phenylalkyl wherein the alkyl moiety has from 1 to 6 carbon atoms and is straight or branched in the presence of a base such as pyridine, quinoline or trialkylamine, such as, triethylamine, which base serves as the solvent, for from 1 to 24 hours at a temperature of from about 25° C to 100° C. The appropriate acid anhydride or acid chloride are known in the art or can be prepared from the corresponding acids by procedures well known in the art.

Compounds employed in the present invention wherein $R_1$ is hydrogen and $R_2$ forms an ester group are prepared from the above obtained 17β,19-diester derivatives by refluxing the diester with one equivalent of sodium bicarbonate or potassium bicarbonate or one-half equivalent of sodium carbonate or potassium carbonate or dilute sodium hydroxide or potassium hydroxide solution in a lower alcohol solvent such as methanol or ethanol and water for about one hour, the reflux temperature depending on the solvent system employed.

Compounds employed in the present invention wherein R is CHO and $R_2$ forms an ester group are prepared by dissolving the above obtained compounds wherein $R_1$ is hydrogen and $R_2$ forms an ester group in acetone cooled to 0° to 10° C and treating the solution with sufficient Jones reagent to effect the oxidation. Jones reagent is prepared by standard procedures using 26.72 grams of chromium trioxide, 23 ml of concentrated sulfuric acid and water to make 100 ml. The Jones reagent can be added to the solution until the reddish brown color persists which requires about 289 ml. Other oxidizing agents can be used, such as, dicyclohexylcarbodiimide in dimethylsulfoxide.

The following specific examples further illustrate the preparation of compounds employed in the instant invention.

EXAMPLE 1

17β,19-Bis(1-oxopropoxy)androst-4-en-3-one

A solution of 10 g of 17β,19-dihydroxyandrost-4-en-3-one which is commercially available and 25 ml of propionic anhydride in 200 ml of pyridine is allowed to stand overnight after which 100 ml of ethanol is added, and the reaction mixture is stirred for 1 hour. The mixture is then poured into one liter of water and the solid product is collected by filtration. The solid is dissolved in ether, dried over magnesium sulfate, filtered and the solvent removed. The residue is dissolved in hot hexane and allowed to cool yielding 17β,19-bis(1-oxopropoxy)androst-4-en-3-one. M.P. 82°–84° C.

EXAMPLE 2

17β,19-Dihydroxyandrost-4-en-3-one

A solution of 150 g of 19-hydroxyandrost-4-en-3-one in 6 liters of ethanol is cooled in an ice bath. To this cold solution is added 13.5 g of potassium borohydride, and the reaction mixture is stirred for two hours at about 0° C after which a second 13.5 g or potassium borohydride is added. Two hours later a third 13.5 g portion of potassium borohydride is added to the reaction mixture which is stirred for an additional 1 hour then poured into 11 liters of water to which 70 ml of acetic acid is added. The ethanol is distilled off under reduced pressure and the aqueous residue cooled to 0° C. The solid which separates is filtered off, dried and dissolved in 25 liters of hot chloroform after which the temperature is adjusted to 25° C. To the chloroform solution is added 250 g of manganese dioxide, and the mixture is stirred for 2 hours then filtered and the solvents removed under reduced pressure. The solid residue is recrystallized from acetonitrile to give 17β,19-dihydroxyandrost-4-en-3-one. M.P. 205°–207° C.

EXAMPLE 3

19-Hydroxy-17β(1-oxopropoxy)androst-4-en-3-one

A solution of 11 g of 17β,19-bis(1-oxopropoxy)androst-4-en-3-one in 2 liters of methanol is treated with 2.5 g of sodium carbonate in 250 ml of water and refluxed for one hour after which the reaction mixture is poured into 10 liters of water, and the solid collected by filtration. The solid is dissolved in methylene chloride, dried over magnesium sulfate, filtered and the solvent removed. The residue is crystallized from acetone-hexane yielding 6 g of 19-hydroxy-17β(1-oxopropoxy)androst-4-en-3-one. M.P. 160°-162° C.

EXAMPLE 4

19-Acetoxyandrost-4-ene-3,17-dione

A solution of 19-hydroxyandrost-4-ene-3,17-dione in acetic anhydride and pyridine is allowed to stand overnight after which the reaction mixture is poured into ice water. The resulting solid is collected, dried and recrystallized from hexane to give 19-acetoxyandrost-4-ene-3,17-dione.

EXAMPLE 5

19-Acetoxy-17β-hydroxyandrost-4-en-3-one

To a solution of 25.6 g of 19-acetoxyandrost-4-ene-3,17-dione in 4 liters of methanol cooled to 0° C is added 3.1 g of sodium borohydride, and the mixture is stirred at 0° C for 1 hour after which 30 ml of acetic acid is added and the methanol removed under reduced pressure. The resulting residue is taken up in ethyl acetate and washed with water. The organic layer is dried over magnesium sulfate, filtered and the solvent removed. The solid residue is dissolved in 2 liters of chloroform treated with 125 g of manganese dioxide and stirred for 2 hours. The reaction mixture is filtered, and the solvent removed under reduced pressure. The residue is chromatographed on alumina using benzene-ether (1:1) as the eluant. The product is recrystallized from acetone-hexane to give 19-acetoxy-17β-hydroxyandrost-4-en-3-one, M.P. 125°-127° C.

EXAMPLE 6

19-Hydroxy-17β(2'-tetrahydropyranyloxy)androst-4-en-3-one

To a solution of 10 g of 19-acetoxy-17β-hydroxyandrost-4-en-3-one in 300 ml of dihydropyran is added a small crystal of p-toluene sulfonic acid. The reaction mixture is allowed to stand overnight after which it is dissolved in ether and extracted with dilute sodium bicarbonate. The ether layer is dried over magnesium sulfate, filtered and the solvent removed. The resulting residue is dissolved in 2 liters of methanol and 2.5 g of sodium bicarbonate in 250 ml of water is added. The methanol solution is refluxed for 1 hour after which the solvent is removed under reduced pressure at 40° C. The residue is covered with water, and the solid crude product collected and recrystallized from ethylacetate yielding 19-hydroxy-17β(2'-tetrahydropyranyloxy)androst-4-en-3-one. M.P. 193°-199° C.

EXAMPLE 7

3-Oxo-17β-hydroxyandrost-4-en-19-al

A solution of 7 g of 19-hydroxy-17β-(2'-tetrahydropyranyloxy)androst-4-en-3-one in 500 ml of acetone is cooled to 10° C and 5.3 ml of Jones reagent is added dropwise. The reaction is stirred for an additional 10 minutes then poured into water and extracted with ethylacetate. The ethylacetate extract is dried over magnesium sulfate, filtered and the solvent removed under reduced pressure. The residue is dissolved in 250 ml of 95% ethanol and 2 ml of concentrated hydrochloridic acid is added. The ethanol solution is refluxed for 1 hour then cooled to room temperature and neutralized with solid sodium carbonate. The neutralized solution is diluted with water and extracted with ethyl acetate. The extract is dried over magnesium sulfate, filtered and the solvent removed leaving a residue which is chromatographed on alumina using 25% ether in benzene as the eluant to give the product 3-oxo-17β-hydroxyandrost-4-en-19-al, M.P. 125°-127° C.

EXAMPLE 8

19-(1-Adamantanylcarbonyloxy)androst-4-ene-3,17-dione

A solution of 22 g of 19-hydroxyandrost-4-ene-3,17-dione, 18 g of 1-adamantanecarboxylic acid chloride, and 29 ml of pyridine in 2.2 liters of toluene is refluxed overnight. The reaction mixture is cooled, and the toluene layer is washed with water, dried over magnesium sulfate and filtered then the solvent is removed. The resulting residue is crystallized from methanol to give 19-(1-adamantanylcarbonyloxy)androst-4-ene-3,17-dione, M.P. 161°-163° C.

EXAMPLE 9

3,17-Dioxoandrost-4-en-19-al

To a solution of 30 g of 19-hydroxyandrost-4-ene-3,17-dione in 3 liters of acetone cooled in an ice bath is added 28 ml of Jones reagent over a 1 hour period. The reaction mixture is stirred for an additional 15 minutes, filtered and the solvent removed under reduced pressure at 35° C. The residue is taken up in a large volume of ether and 1.5 liters of water. The ether layer is collected, dried over magnesium sulfate, filtered and the solvent removed. The residue is crystallized from acetone-hexane to give 3,17-dioxoandrost-4-en-19-al, M.P. 126°-129° C.

EXAMPLE 10

3-Oxo-17β-(1-oxopropoxy)androst-4-en-19-al

To a solution of 14 g of 19-hydroxy-17β-(1-oxopropoxy)androst-4-en-3-one in 1 liter of acetone cooled in an ice bath is added 13.3 ml of Jones reagent over 1 hour after which the reaction mixture is poured into a large volume of water and extracted with ether. The ether extract is dried over magnesium sulfate, filtered and the solvent removed. The residue is crystallized from acetone-hexane to give 3-oxo-17β(1-oxopropoxy)androst-4-en-19-al, M.P. 119°-121° C.

We claim:

1. A method of treating the syptoms of menopause in a patient in need thereof which comprises administering to said patient a compound of the formula in an amount effective to treat the symptoms of menopause:

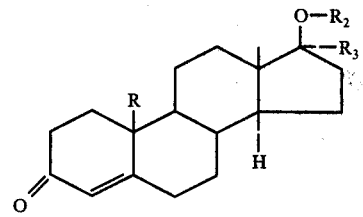

wherein R is —CHO or —CH$_2$OR$_1$; each of R$_1$ and R$_2$ is hydrogen, alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched or cycloalkylcarbonyl wherein the cycloalkyl moiety has from 5 to 10 carbon atoms; R$_3$ is hydrogen; or $R_2$ and $R_3$ together form a double bond between the 17- position carbon atom and the oxygen atom.

2. The method of claim 1 wherein the compound is administered orally in an amount of from 0.01 up to 3.0 mg/kg.

3. The method of claim 1 wherein the compound is administered orally in an amount of from 0.1 to 1.0 mg/kg.

4. The method of claim 1 wherein the compound is administered parenterally in an amount of from 0.01 up to 1.0 mg/kg.

5. The method of claim 1 wherein the compound is administered parenterally in an amount of from 0.1 to 0.5 mg/kg.

6. The method of claim 1 wherein the compound is administered as a topical preparation containing from 0.001% to 5% of the compound.

7. The method of claim 1 wherein the compound is administered as a topical preparation containing from 0.005% to 1% of the compound.

8. The method of claim 1 wherein R is —CHO.

9. The method of claim 8 wherein $R_2$ and $R_3$ together form a double bond between the 17- position carbon atom and the oxygen atom.

10. The method of claim 9 wherein the compound is 3,17-dioxoandrost-4-en-19-al.

11. The method of claim 1 wherein R is —CH$_2$OR$_1$.

12. The method of claim 11 wherein $R_2$ and $R_3$ together form a double bond between the 17- position carbon atom and the oxygen atom.

13. The method of claim 12 wherein the compound is 19-hydroxyandrost-4-ene-3,17-dione.

14. The method of claim 1 wherein the symptoms are selected from dehydration of the skin, atrophic vaginitis and hot flashes.

15. A method of treating osteoporosis in a patient in need thereof which comprises administering to said patient a compound of the formula in an amount effective to treat osteoporosis:

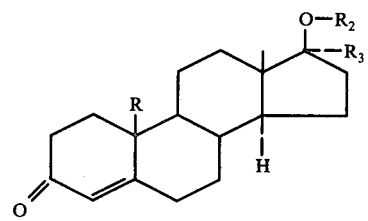

wherein R is —CHO or —CH$_2$OR$_1$; each of $R_1$ and $R_2$ is hydrogen, alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched or cycloalkylcarbonyl wherein the cycloalkyl moiety has from 5 to 10 carbon atoms; $R_3$ is hydrogen; or $R_2$ and $R_3$ together form a double bond between the 17-position carbon atom and the oxygen atom.

16. The method of claim 15 wherein the patient is menopausal.

17. The method of claim 16 wherein the compound is 3,17-dioxoandrost-4-en-19-al.

18. The method of claim 16 wherein the compound is 19-hydroxyandrost-4-ene-3,17-dione.

* * * * *